US005229522A

United States Patent [19]

Mathiaparanam

[11] Patent Number: 5,229,522

[45] Date of Patent: Jul. 20, 1993

[54] BIS-(INDOLYL)ETHYLENES: PROCESS FOR THEIR PREPARATION

[75] Inventor: Ponnampalam Mathiaparanam, Appleton, Wis.

[73] Assignee: Appleton Papers Inc., Appleton, Wis.

[21] Appl. No.: 576,765

[22] Filed: Sep. 4, 1990

Related U.S. Application Data

[62] Division of Ser. No. 320,642, Mar. 8, 1989, Pat. No. 4,996,328.

[51] Int. Cl.$^5$ .................. C07D 209/56; C07D 209/02; C07D 401/06; C07D 417/14

[52] U.S. Cl. .................................... 548/427; 548/450; 548/455; 544/60; 544/61; 544/62; 544/142; 544/143; 544/144; 546/200; 546/201

[58] Field of Search ........................ 548/427, 450, 455; 544/60, 61, 62, 142, 143, 144; 546/200, 201

[56] References Cited

U.S. PATENT DOCUMENTS

| | | | |
|---|---|---|---|
| 2,155,447 | 4/1939 | Roh et al. | 548/455 |
| 4,419,511 | 12/1983 | Raue | 548/455 |
| 4,565,757 | 1/1986 | Chalk et al. | 548/455 |
| 4,599,300 | 7/1986 | Tanaka et al. | 548/455 |
| 4,600,776 | 7/1986 | Meisel et al. | 548/455 |
| 4,795,736 | 1/1989 | Hung et al. | 548/427 |
| 4,902,806 | 2/1990 | Psaar | 548/455 |

FOREIGN PATENT DOCUMENTS 0970601 4/1963 United Kingdom .

OTHER PUBLICATIONS

Kiang et al. J. Chem. Soc. 594 (1953).
Angeli et al. Chem. Abstracts 2, 1833 (1908).
Borsche et al. Chem. Abstracts 37; 37549 (1943).
Saxon; J. Chem. Soc. 3592 (1952).

*Primary Examiner*—Johann Richter

*Attorney, Agent, or Firm*—Benjamin Mieliulis

[57] ABSTRACT

Novel bis-(indolyl)ethylenes, process for their production and record systems utilizing such bis-(indolyl)ethylene chromogens are described.

Bis-(indolyl)ethylenes of the following general formula are prepared:

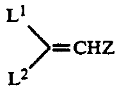

(I)

wherein each $L^1$ and $L^2$ is the same or different and is each independently selected from indole moieties (J1) through (J4) ($L^1$ need not be the same as $L^2$),

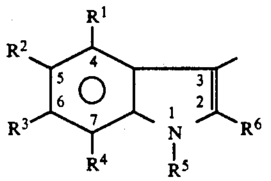

(J1)

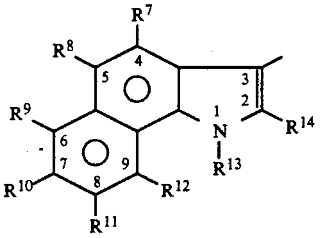

(J2)

wherein Z is hydrogen, alkyl ($C_1$-$C_8$), substituted or unsubstituted aryl, aralkyl, aroxyalkyl, alkoxyalkyl or halogen.

4 Claims, No Drawings

BIS-(INDOLYL)ETHYLENES: PROCESS FOR THEIR PREPARATION

This application is a division of Ser. No. 07/320,642 filed Mar. 8, 1989 now U.S. Pat. No. 4,996,328.

FIELD OF INVENTION

1. Background of Invention

This invention relates to bis-(indolyl)ethylenes and methods for their production. More particularly, this invention relates to chromogenic compounds which can give intense colors when reacted with an electron accepting coreactant material. More specifically, this invention relates to methods for the production of such chromogenic compounds and novel pressure-sensitive or heat-sensitive mark-forming record systems incorporating such compounds. As used in mark-forming systems, marking in desired areas on support webs or sheets may be accomplished by effecting selective localized reactive contact between the chromogenic material and the electron-accepting material on or in such web or sheet, such material being brought thereto by transfer or originally there in situ. The selective reactive contact forms colored images in the intended image marking areas.

2. Description of Related Art

Several divinyl phthalide chromogenic compounds (C1) [(C) $L^1$, $L^2$=substituted phenyl] (read as Compound Cl arrived at by referring to formula C wherein $L^1$ and $L^2$ are as stated) have been prepared by the condensation of ethylenes (A1) [(A) $L^1$, $L^2$=substituted phenyl] with phthalic anhydrides (B1) [(B) Each Halogen is independently Cl or Br] in acetic anhydride (Sheldon Farber, U.S. Pat. Nos. 4,020,056, 4,022,771, 4,107,428, 4,119,776;)

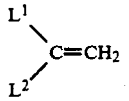

(A)

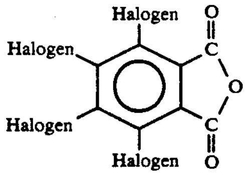

(B)

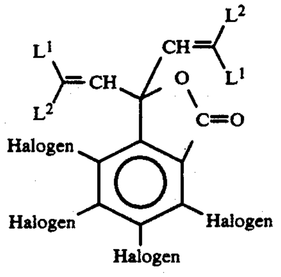

(C)

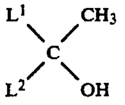

(D)

-continued

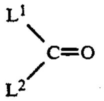

(E)

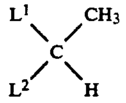

(F)

Substituted ethylenes (A1) or their precursors (D1) [(D) $L^1$, $L^2$=substituted phenyl] were prepared by the reaction of methylmagnesium bromide (also known as methyl Grignard reagent) with ketones (E1) [(E) $L^1$, $L^2$=substituted phenyl]. The use of a Grignard reaction to prepare (A1) imposes severe restrictions on the scaleup synthesis of (A1) and consequently on the manufacture of divinyl phthalides (C1).

In another synthetic approach, the alcohol (D1) was obtained by reacting the ethane (F1) [(F) $L^1$, $L^2$=substituted phenyl] with lead peroxide in either nitric acid or formic acid; and the substituted ethylene (A) was obtained from (D1) by dehydration [Yamada Kagaku, Japan Kokai 1988-8360, filed June 30, 1986].

When indole was heated with acetic anhydride containing 10% acetic acid a bis-(indolyl)ethylene (A2) [(A) $L^1$, $L^2$=1-acetylindole-3-yl] Apparently was obtained as a by-product in 5–10% yield (J. E. Saxton, J. Chem. Soc., 3592 (1952)].

Substituted (2- and 1,2-) indoles when reacted with acetyl cyanide in the presence of hydrogen chloride yielded 1-cyano-1,1-di(3-indolyl)ethanes (G) and apparently some of these products may be converted to bis-(indolyl)ethylenes (H) by heating them under vacuum either alone or with soda lime. In some cases, dependent on certain select substituents M and W, (G) may yield some (H) type compounds on refluxing with aqueous-ethanolic 10% potassium hydroxide [A. K. Kiang and F. G. Mann, J. Chem., Soc., 594 (1953)].

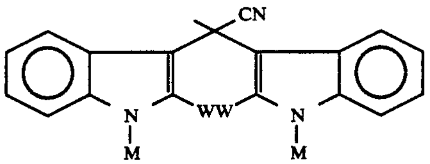

(G)

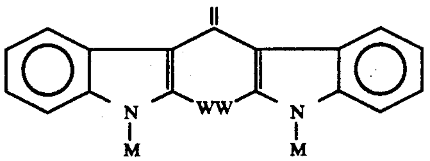

(H)

M=H, Ph

W=Me, Ph

Bis-(indolyl)ethylene (H1) [(H) M=H and W=Me] was speculated to be a product (m.p. 203° C.) from the reaction of 2-methylindole with ethyl acetate and sodium ethoxide. No other data were given to substantiate the structure [A. Angeli and G. Marchetti, Atti. Accad. Lincei, 16 (II), 179 (1907)].

In another report (W. Borsche and H. Groth, Annalen, 549, 238 (1941)], 2-methylindole when boiled with acetyl chloride formed a product that on treatment with alkali gave a pseudobase, ($C_{20}H_{18}N_2$, pale rose, m.p. 208° C.). The pseudobase was suggested to be 1-(2-methyl-indole-3-yl)-1-(2-methyl-3-indolidene)ethane (H2). Again, insufficient data precludes the substantiation of this structure. Furthermore, similar structure was proposed for the pseudobase obtained by substituting 2-phenylindole for 2-methylindole.

(H2)

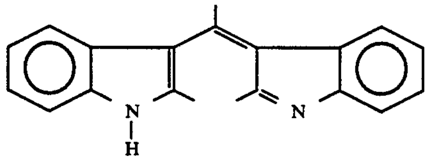

SUMMARY OF THE INVENTION

A novel method for producing bis-(indolyl)ethylenes and novel bis-(indolyl)ethylene compounds are described along with record systems incorporating such compounds.

In the process of the invention bis-(indolyl)ethylenes of the following general formula are prepared:

(I)

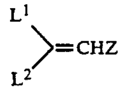

wherein each $L^1$ and $L^2$ is the same or different and is each independently selected from indole moieties (J1) through (J4) ($L^1$ need not be the same as $L^2$), wherein Z is hydrogen, alkyl ($C_1$–$C_8$), substituted or unsubstituted aryl, aralkyl, aroxyalkyl, alkoxyalkyl and halogen, (J1)

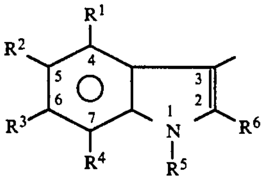

(J2)

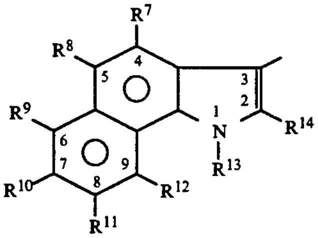

(J3)

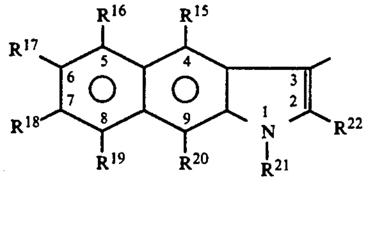

-continued (J4)

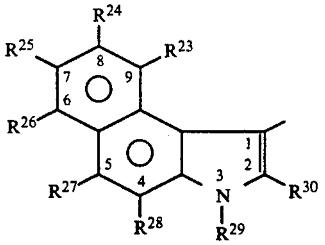

wherein in (J1) through (J4) above, each of $R^5$, $R^6$, $R^{13}$, $R^{14}$, $R^{21}$, $R^{22}$, $R^{29}$ and $R^{30}$ need not be the same and is each independently selected from hydrogen, alkyl ($C_1$–$C_8$), cycloalkyl, aroxyalky, alkoxyalkyl, and substituted or unsubstituted aryl, such as phenyl, naphthyl, or heterocyclyl.

Each of $R^1$, $R^2$, $R^3$, $R^4$, $R^7$, $R^8$, $R^9$, $R^{10}$, $R^{11}$, $R^{12}$, $R^{15}$, $R^{16}$, $R^{17}$, $R^{18}$, $R^{19}$, $R^{20}$, $R^{23}$, $R^{24}$, $R^{25}$, $R^{26}$, $R^{27}$ and $R^{28}$ need not be the same and is each independently selected from hydrogen, alkyl ($C_1$–$C_8$), cycloalkyl, substituted or unsubstituted aryl, halogen, alkoxy ($C_1$–$C_8$), aroxy, cycloalkoxy, dialkylamino including symmetrical and unsymmetrical alkyl groups with one to eight carbon, alkylcycloalkylamino, dicycloalkylamino,

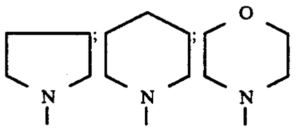

and

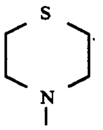

The bis(indolyl)ethylenes (I) are formed by three major routes. The first route uses the corresponding indoles, acid anhydride (such as $(ZCH_2CO)_2O$, Z as defined elsewhere) and Lewis Acid such as zinc chloride or other electron acceptor preferably in approximately 1:1:0.5 molar ratios respectively in a suitable solvent. The second route uses the corresponding indoles with acid chloride (such as $ZCH_2COCl$, Z as defined earlier) preferably in approximately 1:(0.15–2.0) molar amounts at temperatures (15°–75° C.) with or without solvent. The third route involves a condensation of a component selected from (K1) through (K4) with an indole selected from (J1) through (J4) in the presence of a Vilsmeier reagent (such as phosphoryl chloride, phosgene, oxalyl chloride, benzoyl chloride, alkanesulfonyl chloride, arenesulfonyl chloride, alkyl chloroformate and arylchloroformate) with or without solvent. Moreover, the third route can be used to prepare unsymmetrical indolyl ethylenes (i.e. (I) with different $L^1$ and $L^2$).

(K1)

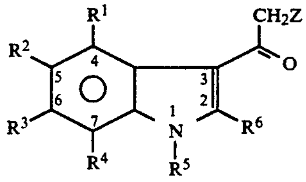

-continued

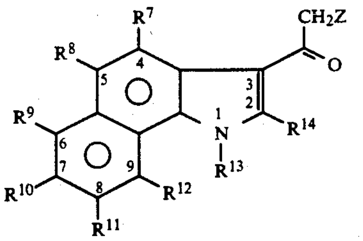

(K2)

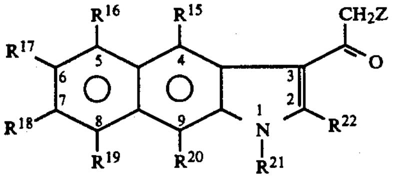

(K3)

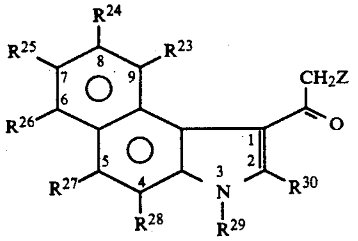

(K4)

In (K1) through (K4) above, each of $R^5$, $R^6$, $R^{13}$, $R^{14}$, $R^{21}$, $R^{22}$, $R^{29}$ and $R^{30}$ need not be the same and is each independently selected from hydrogen, alkyl ($C_1$–$C_8$), cycloalkyl, alkylaroxy, alkylalkoxy, and substituted or unsubstituted aryl, such as phenyl, naphthyl, or heterocyclyl.

Each of $R^1$, $R^2$, $R^3$, $R^4$, $R^7$, $R^8$, $R^9$, $R^{10}$, $R^{11}$, $R^{12}$, $R^{15}$, $R^{16}$, $R^{17}$, $R^{18}$, $R^{19}$, $R^{20}$, $R^{23}$, $R^{24}$, $R^{25}$, $R^{26}$, $R^{27}$ and $R^{28}$ need not be the same and is each independently selected from hydrogen, alkyl ($C_1$–$C_8$), cycloalkyl, substituted or unsubstituted aryl, halogen, alkoxy ($C_1$–$C_8$), aroxy, cycloalkoxy, dialkylamino including symmetrical and unsymmetrical alkyl groups with one to eight carbon, alkylcycloalkylamino, dicycloalkylamino,

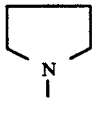;
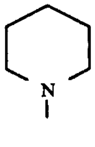;
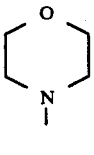
and
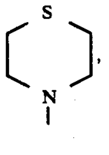,

Z is hydrogen, alkyl ($C_1$–$C_8$), substituted or unsubstituted aryl, aralkyl, aroxyalkyl, alkoxyalkyl and halogen.

(In this application Z is sometimes interchangeably written as Z).

DETAILED DESCRIPTION

This invention teaches three processes for the preparation of chromogenic compounds which in color form have absorbance in the visible region of the spectrum at approximately 400–700 nm and thus are eligible for use in pressure-sensitive and thermal recording systems. Compounds which are chromogenic and absorptive in the visible region of the spectrum have commercial utility by being capable, when imaged, of being detected by optical reading machines.

More particularly, this invention describes novel pressure-sensitive and thermal record systems and a method for the preparation of substantially colorless but colorable chromogenic compounds eligible for use in pressure-sensitive and thermal recording systems. Advantageously recording systems utilizing these compounds can be read by optical reading machines, particularly those capable of reading for the wavelength range of 400–700 nm.

The colorable chromogenic compounds of the invention, can be combined with other chromogenic materials covering other or wider spectral ranges and can be used in pressure-sensitive and thermal recording systems to provide images which absorb over wider ranges of the electromagnetic spectrum. The commercial significance is that a larger assortment of available optical readers can thus be effectively useful with such imaged record systems.

The chromogenic compounds of the invention also find use in photosensitive printing material, typewriter ribbons, inks and the like.

Specifically the process of the invention relates to the preparation of bis-(indolyl)ethylenes. These compounds are substantially colorless or slightly colored solids but can be converted to colored forms upon reactive contact with an electron accepting material. The compounds of the invention in imaged or colored form are typically visibly colored and can be detected by conventional optical readers capable of detecting in the wavelength range of 400–700 nm.

In the process of the invention bis(indolyl)ethylenes of the following general formula are prepared:

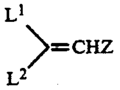

(I)

wherein each $L^1$ and $L^2$ is the same or different and each is independently selected from indole moieties (J1) through (J4) ($L^1$ need not be the same as $L^2$), wherein Z is hydrogen, alkyl ($C_1$–$C_8$), substituted or unsubstituted aryl, aralkyl, aroxyalkyl, alkoxyalkyl and halogen,

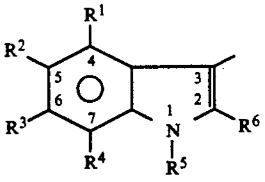

(J1)

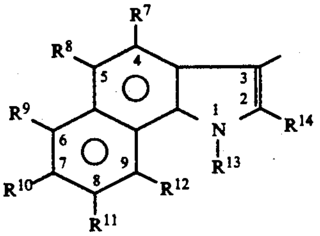

(J2)

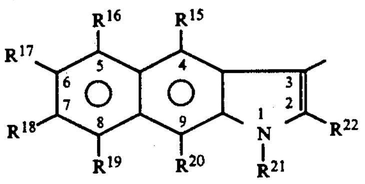

(J3)

-continued

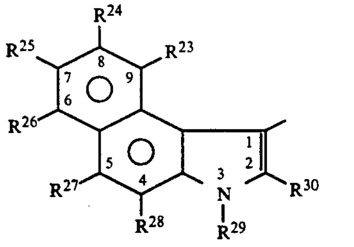

(J4)

wherein in (J1) through (J4) above, each of $R^5$, $R^6$, $R^{13}$, $R^{14}$, $R^{21}$, $R^{22}$, $R^{29}$ and $R^{30}$ need not be the same and is independently selected from hydrogen, alkyl ($C_1$–$C_8$), cycloalkyl, aroxy, alkylalkoxy, and substituted or unsubstituted aryl, such as phenyl, naphthyl, or heterocyclyl.

Each of $R^1$, $R^2$, $R^3$, $R^4$, $R^7$, $R^8$, $R^9$, $R^{10}$, $R^{11}$, $R^{12}$, $R^{15}$, $R^{16}$, $R^{17}$, $R^{18}$, $R^{19}$, $R^{20}$, $R^{23}$, $R^{24}$, $R^{25}$, $R^{26}$, $R^{27}$ and $R^{28}$ need not be the same and is each independently selected from hydrogen, alkyl ($C_1$–$C_8$), cycloalkyl, substituted or unsubstituted aryl, halogen, alkoxy ($C_1$–$C_8$), aroxy, cycloalkoxy, dialkylamino including symmetrical and unsymmetrical alkyl groups with one to eight carbon, alkylcycloalkylamino, dicycloalkylamino,

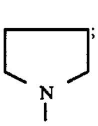; 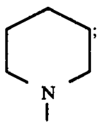; 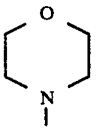 and 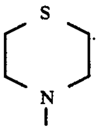.

It is advantageous for clarity of discussion to also establish the following subgroup of formula I compound for the special case when $L_1$ and $L_2$ are simultaneously (J1). Higher precision is then advantageous to draw clear demarcation between the invention and the art. Thus, for $L_1$ and $L_2$ being simultaneously (J1) the following subgroup is established. (For clarity note that "simultaneously (J1)" contemplates allowing each (J1) the full panoply of variables available for J1, thus $L_1$ and $L_2$ when both are (J1) however need not be precisely identical in that the $R^1$ through $R^6$ variables can differ.)

The above-referenced subgroup is as follows:

Chromogenic bis(indolyl)ethylene of the formula

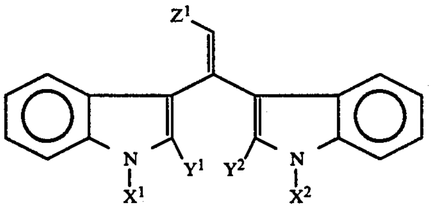

wherein $Z^1$ is hydrogen, alkyl ($C_1$–$C_8$) substituted or unsubstituted aryl, aralkyl, aroxyalkyl, alkoxyalkyl and halogen;

wherein $X^1$ and $X^2$ need not be the same and is each independently selected from alkyl ($C_1$–$C_8$), cycloalkyl, alkylaroxy, alkylalkoxy, substituted aryl and unsubstituted aryl;

wherein $Y^1$ and $Y^2$ need not be the same and is each independently selected from alkyl ($C_1$–$C_8$), and unsubstituted aryl;

with the proviso that $X^1$, $X^2$, $Y^1$ and $Y^2$ are not all simultaneously unsubstituted aryl;

with the proviso that $Y^1$ and $Y^2$ are not simultaneously unsubstituted aryl when $X^1$ and $X^2$ are both methyl.

With the above subgroup established it is convenient as to the formula I compounds to attach the proviso that when $L^1$ and $L^2$ are simultaneously (J1), that $R^1$, $R^2$, $R^3$ and $R^4$ are not all hydrogen simultaneously. Said proviso does not apply as to the three methods disclosed to produce the formula I compounds or the record materials, in that the method and record material aspect of the invention is of broader scope and applicability than just the specific new compounds (Formula I and the above subgroup) recited herein.

According to the first process of the invention, the bis-(indolyl)ethylenes, (I) for example, are prepared by condensing the indoles (J1) through (J4) with acid anhydride [$(ZCH_2CO)_2O$)] in the presence of compounds belonging to:

Carboxylic Acids (e.g. Acetic Acid); or

Sulfonic Acids (e.g. p-Toluenesulfonic Acid); or

Acid Chlorides (e.g. Benzoyl Chloride); or

Lewis Acids (e.g. Zinc Chloride, Boron Trifluoride)

in solvents, preferably organic, or more preferably the halogenated organic solvents such as 1,2-dichloroethane and chlorobenzene and the like.

Specifically, the indole (J5) was refluxed with zinc chloride and acetic anhydride in 1,2-dichloroethane. After one hour, the starting material had disappeared and the reaction mixture contained the bis-(indolyl-)ethylene (I1) [(I) $L^1=L^2=$ 1-ethyl-2-methyl-3-indolyl, Z=H] as the major product; and (K5) as the minor product. Further studies on this reaction revealed that the yield of (I1) depended on the relative molar amounts of indole (J5), acetic anhydride and zinc chloride. The results of these studies are summarized in Table 1.

TABLE 1

| Entry | Indole (J1) (Mole) | Acetic Anhydride (Mole) | Zinc Chloride (Mole) | Yield (I1) (%) |
|---|---|---|---|---|
| 1 | 0.10 | 0.05 | 0.10 | Incomplete Reaction |
| 2 | 0.10 | 0.10 | 0.10 | 47.0 |
| 3 | 0.10 | 0.10 | 0.15 | 59.0 |
| 4 | 0.10 | 0.10 | 0.05 | 60.0 |

Reaction Conditions: Solvent, 1,2-dichloroethane; reflux 2 hours.

From Table 1, it seems that equimolar amounts of indole (J5) and acetic anhydride are preferred for complete reaction and that half the molar amount of zinc chloride is sufficient to carry out the reaction (of Entry 4). Using these reactions, several bis-(indolyl)ethylenes (I) were prepared and some examples are included in Table 3.

In the second process, bis-(indolyl)ethylenes (I) are prepared by reacting the indoles (J1) through (J4) with acid chloride ($ZCH_2COCl$) with or without solvent in the temperature range 15°–75° C.

This process was studied in detail using the indole (J5) and acetyl chloride ($CH_3COCl$) by varying the reaction conditions and the results are summarized in Table 2.

TABLE 2

| Entry | Acetylchloride (Mole) | Solvent | Temperature (°C.) | Time (Hours) | Yield (I1) (%) |
|---|---|---|---|---|---|
| 1 | 0.015 | $(CH_3CO)_2O$ | 50–52 | 14 | 88.0 |

TABLE 2-continued

| Entry | Acetylchloride (Mole) | Solvent | Temperature (°C.) | Time (Hours) | Yield (I1) (%) |
|---|---|---|---|---|---|
| 2 | 0.025 | $(CH_3CO)_2O$ | 50-52 | 8 | 96.0 |
| 3 | 0.05 | $(CH_3CO)_2O$ | 15-20* | 24 | 49.0 |
| 4 | 0.05 | $(CH_3CO)_2O$ | 50-52 | 7 | 95.0 |
| 5 | 0.10 | $(CH_3CO)_2O$ | 50-52 | 3 | 95.0 |
| 6 | 0.12 | $ClCH_2CH_2Cl$ | 45-50 | 30 | 78.0 |
| 7 | 0.06 | $ClCH_2CH_2Cl$ | 65-75 | 48 | 41.0 |
| 8 | 0.10 | Toluene | 15-20* | 20 | 86.0 |
| 9 | 0.12 | Toluene | 50-55 | 20 | 35.0 |
| 10 | 0.10 | Diglyme | 15-20* | 20 | 65.0 |
| 11 | 0.12 | None | 15-20* | 20 | 76.0 |
| 12 | 0.20 | None | 15-20* | 20 | 76.0 |

Amount of (J5) used, 0.1 mole. *Room temperature. Solvent (15 ml). For a sample procedure, see Example 3.

From Table 2, it seems that acetic anhydride is the best solvent for the reaction and that varying amounts of acetyl chloride (0.015–0.1 mole) (entries 2, 4 and 5) can be used with variable reaction times at 50°-52° C. to get very good yields of (I1). The reaction time is inversely proportional to the acetyl chloride concentration. Several bis-(indolyl)ethylenes (I) were prepared using this process and some examples are included in Table 3.

In the third process for the production of bis-(indolyl-)ethylenes, the acylindoles (K1) through (K4) are condensed with indoles (J1) through (J4) using Vilsmeier reagents (such as phosphoryl chloride, phosgene, oxalyl chloride, benzoyl chloride, alkane or arenesulfonylchloride and alkyl or arylchloroformate) with or without solvent. This process is very versatile because symmetrical as well as unsymmetrical indolyl ethylenes can be produced.

This condensation reaction was studied in detail using the acetylindole (K5) and the indole (J6) using phosphoryl chloride as a condensing agent in 1,2-dichloroethane as solvent. A solution of acetylindole (K5) in 1,2-dichlorethane was cooled in an ice/salt bath and phosphoryl chloride was added slowly, keeping the temperature of the reaction mixture between 0° and 5° C. during the addition. This low temperature was preferred during the initial stages of this reaction to minimize the formation of unwanted byproducts. After 30 minutes stirring while the reaction mixture warmed to room temperature, indole (J6) in 1,2-dichloroethane was added. The reaction mixture was stirred overnight at room temperature and gas chromatographic analysis indicated that the condensation, though not complete, had taken place. The condensation reaction was driven to completion by refluxing the reaction mixture for one hour. The product, unsymmetrical indolylethene [Table 3, Entry 22], was isolated in good yield (74%, Example 11).

Using a similar procedure discussed above, another unsymmetrical indolylethylene [Table 3, Entry 21] was also prepared in good yield (80%, Example 10).

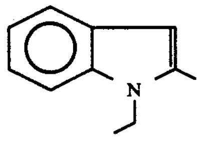
(J5)

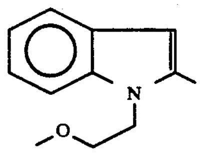
(J6)

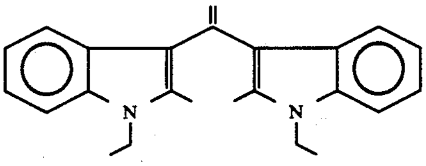
(I1)

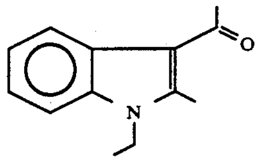
(K5)

TABLE 3

| Entry | Compound | M.P. (°C.) | Color |
|---|---|---|---|
| 1 | 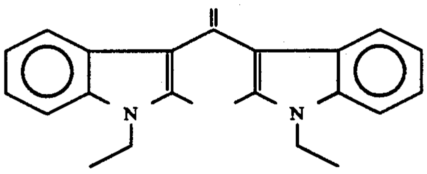 | 179-181 | Pale Yellow |
| 2 | 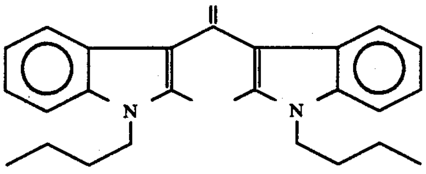 | Oil | Pale Brown |

TABLE 3-continued
| Entry | Compound | M.P. (°C.) | Color |
|---|---|---|---|
| 3 | 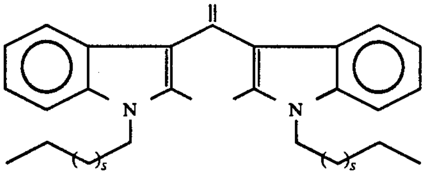 | Oil | Pale Brown |
| 4 | 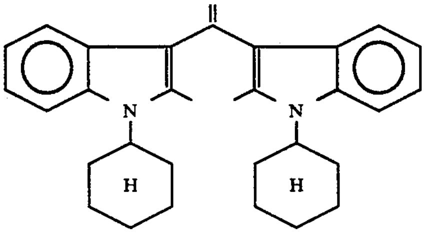 | 205-207 | Grey |
| 5 | 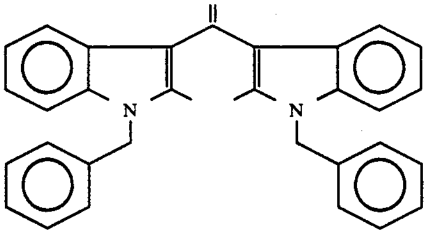 | 148-151 | Yellow |
| 6 | 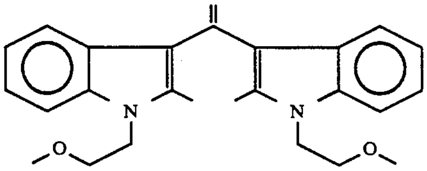 | 85-86 | Pale Yellow |
| 7 | 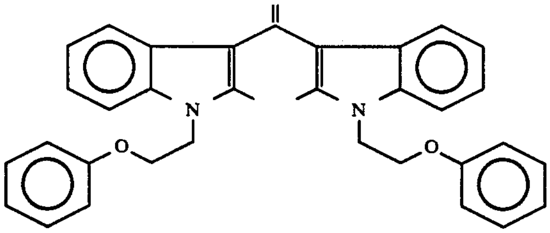 | 65-67 | Yellow |
| 8 | 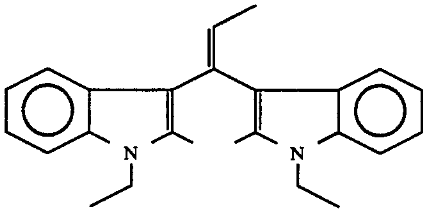 | 109-110 | Beige |

TABLE 3-continued
| Entry | Compound | M.P. (°C.) | Color |
|---|---|---|---|
| 9 | 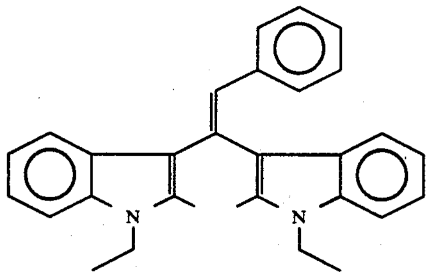 | 157–159 | Pale Yellow |
| 10 | 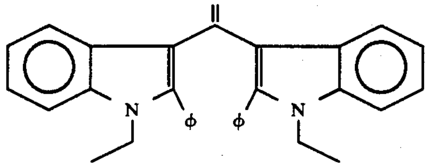 | 165–167 | Pale Brown |
| 11 | 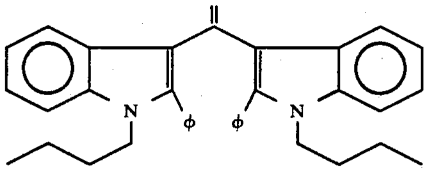 | Oil | Pale Brown |
| 12 | 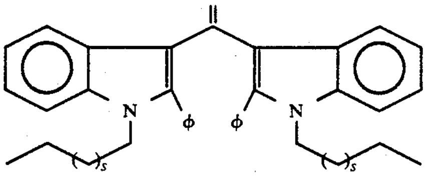 | Oil | Pale Brown |
| 13 | 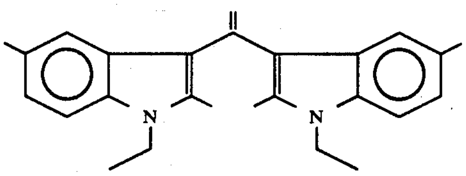 | 125–127 | Grey |
| 14 | 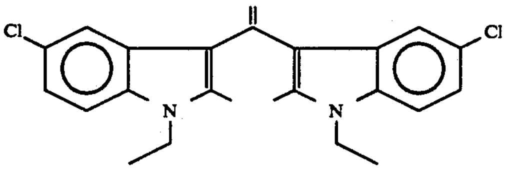 | 138–140 | White |
| 15 | 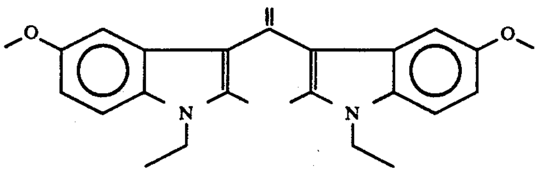 | 100–101 | Pale Orange |

TABLE 3-continued
| Entry | Compound | M.P. (°C.) | Color |
|---|---|---|---|
| 16 | 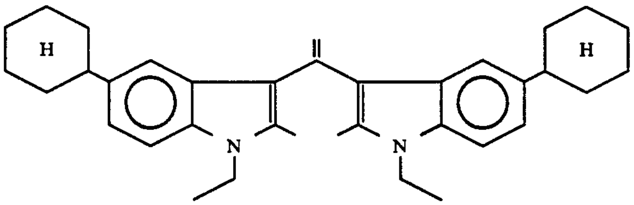 | 156-158 | White |
| 17 | 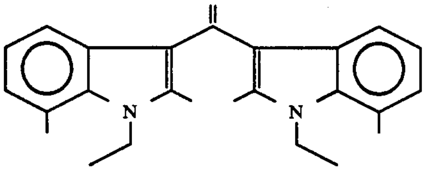 | 160-161 | Grey |
| 18 | 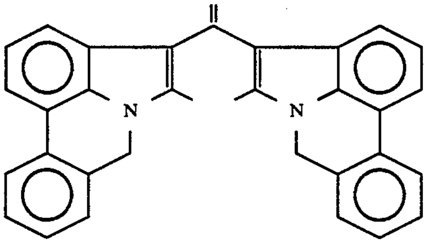 | 156-157 | White |
| 19 | 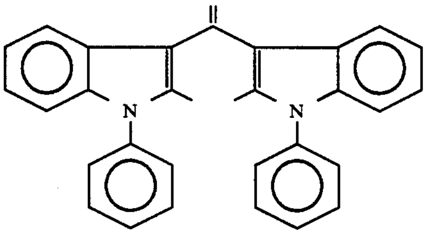 | 150-154 | Yellow |
| 20 | 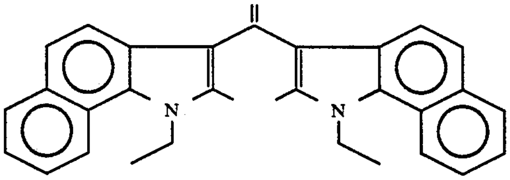 | 182-184 | Pale Brown |
| 21 | 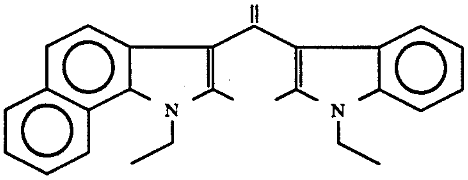 | 138-140 | Yellow |
| 22 | 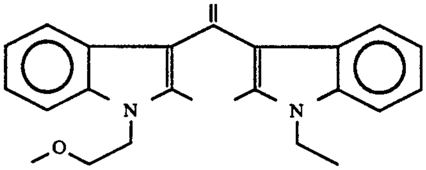 | 123-125 | Pale Yellow |
φ = phenyl.

All of these processes discussed so far for the production of bis-(indolyl)ethylenes (I) are very conducive to scale-up.

In forming pressure sensitive or heat sensitive mark forming record systems with the bis-(indolyl)ethylenes of the invention, the eligible acidic, or electron acceptor materials include, but are not limited to, acid clay substances such as attapulgite, bentonite and montmorillonite and treated clays such as silton clay as disclosed in U.S. Pat. Nos. 3,622,364 and 3,753,761, phenols and diphenols as disclosed in U.S. Pat. No. 3,539,375, aromatic carboxylic acids such as salicylic acid, metal salts of aromatic carboxylic acids as disclosed in U.S. Pat. No. 4,022,936 and acidic polymeric material such as phenol-formaldehyde polymers as disclosed in U.S. Pat. No. 3,672,935 and oil-soluble metal salts of phenol-formaldehyde polymers as disclosed in U.S. Pat. No. 3,732,120. The compounds of this invention are useful as color formers in recording materials such as, for example, pressure-sensitive copying paper, thermally-responsive record material, electro heat-sensitive recording paper and thermal ink.

Pressure-sensitive copying paper systems provide a marking system and can be assembled by disposing on and/or within sheet support material unreacted mark-forming components and a liquid solvent in which one or both of the mark-forming components is soluble, said liquid solvent being present in such form that it is maintained isolated by a pressure-rupturable barrier from at least one of the mark-forming components until application of pressure causes a breach of the barrier in the area delineated by the pressure pattern. The mark-forming components are thereby brought into reactive contact, producing a distinctive mark.

The pressure-rupturable barrier, which maintains the mark-forming components in isolation, preferably comprises microcapsules containing liquid solvent solution. The microencapsulation process utilized can be chosen from the many known in the art. Well known methods are disclosed in U.S. Pat. Nos. 2,800,457; 3,041,289; 3,533,958; 3,755,190; 4,001,140 and 4,100,103. Any of these and other methods are suitable for encapsulating the liquid solvent containing the chromogenic compounds of this invention.

The chromogenic compounds of this invention are particularly useful in pressure-sensitive copying paper systems which incorporate a marking liquid comprising a vehicle in which is dissolved a complement of several colorless chromogenic compounds each exhibiting its own distinctive color on reaction with an eligible acidic record material sensitizing substance. Such marking liquids are disclosed in U.S. Pat. No. 3,525,630.

Thermally-responsive record material systems provide a marking system of color-forming components which relies upon melting or subliming one or more of the components to achieve reactive, color-producing contact. The record material includes a substrate or support material which is generally in sheet form. The components of the color-forming system are in a substantially contiguous relationship, substantially homogeneously distributed throughout a coated layer material deposited on the substrate. In manufacturing the record material, a coating composition is prepared which includes a fine dispersion of the components of the color-forming system, polymeric binder material, surface active agents and other additives in an aqueous coating medium.

The chromogenic compounds of this invention are useful in thermally-responsive record material systems either as single chromogenic compounds or in mixtures with other chromogenic compounds. Examples of such systems are given in U.S. Pat. Nos. 3,539,375 and 4,181,771.

Thermally-responsive record material systems are well known in the art and are described in many patents, for example U.S. Pat. Nos. 3,539,375; 3,674,535; 3,746,675; 4,151,748; 4,181,771; and 4,246,318 which are hereby incorporated by reference. In these systems, basic chromogenic material and acidic color developer material are contained in a coating on a substrate which, when heated to a suitable temperature, melts or softens to permit said materials to react, thereby producing a colored mark.

In the field of thermally-responsive record material, thermal sensitivity (response) is defined as the temperature at which a thermally-responsive record material produces a colored image of satisfactory intensity (density). Background is defined as the amount of coloration of a thermally-responsive record material before imaging and/or in the unimaged areas of an imaged material. The ability to maintain the thermal sensitivity of a thermally-responsive record material while reducing the background coloration is a much sought after and very valuable feature.

One of the uses for thermally-responsive record material which is enjoying increasing importance is facsimile reproduction. Alternative terms for facsimile are telecopying and remote copying. In the facsimile system, images transmitted electronically are reproduced as hard copy. One of the important requirements for thermally-responsive record material to be used in facsimile equipment is that it have good (low coloration) background properties.

Increases in the sensitivity of thermally-responsive record material have been achieved through the incorporation of a phenylhydroxynaphthoate compound or a hydroxyanilide compound in the color-forming composition along with the chromogenic material and developer material as disclosed in U.S. Pat. No. 4,470,057 or U.S. Pat. No. 4,535,347, respectively, by Kenneth D. Glanz. Such sensitizer materials can be advantageously used in combination with the present invention.

The record material includes a substrate or support material which is generally in sheet form. For purposes of this invention, sheets also mean webs, ribbons, tapes, belts, films, cards and the like. Sheets denote articles having two large surface dimensions and a comparatively small thickness dimension. The substrate or support material can be opaque, transparent or translucent and could, itself, be colored or not. The material can be fibrous including, for example, paper and filamentous synthetic materials. It can be a film including, for example, cellophane and synthetic polymeric sheets cast, extruded, or otherwise formed. The gist of this invention resides in the color-forming composition coated on the substrate. The kind or type of substrate material is not critical.

Although not required to practice and demonstrate the beneficial properties of the claimed invention, the inclusion of certain sensitizing materials in the color-forming system provides a further improvement in properties, especially increases in sensitivity. Materials such as phenyl-1-hydroxy-2-naphthoate, stearamide, 1,2-diphenoxyethane and p-hydroxyoctadecananilide are useful as such sensitizing materials.

The components of the color-forming system are in a contiguous relationship, substantially homogeneously distributed throughout the color-forming system, preferably in the form of a coated layer deposited on the substrate. In manufacturing the record material, a coating composition is prepared which includes a fine dispersion of the components of the color-forming system, polymeric binder material, surface active agents and other additives in an aqueous coating medium. The composition can additionally contain inert pigments, such as clay, talc, aluminum hydroxide, calcined kaolin clay and calcium carbonate; synthetic pigments, such as urea-formaldehyde resin pigments; natural waxes such as carnauba wax; synthetic waxes; lubricants such as zinc stearate; wetting agents and defoamers.

The color-forming system components are substantially insoluble in the dispersion vehicle (preferably water) and are ground to an individual average particle size of between about 1 micron to 10 microns, preferably about 1 to 3 microns. The polymeric binder material is substantially vehicle soluble, although latexes are also eligible in some instances. Preferred water-soluble binders include polyvinyl alcohol, hydroxy ethylcellulose, methylcellulose, hydroxypropylmethylcellulose, starch, modified starches, gelatin and the like. Eligible latex materials include polyacrylates, polyvinylacetates, polystyrene, and the like. The polymeric binder is used to protect the coated materials from brushing and handling forces occasioned by storage and use of the thermal sheets. Binder should be present in an amount to afford such protection and in an amount less than will interfere with achieving reactive contact between color-forming reactive materials.

Coating weights can effectively be about 3 to about 9 grams per square meter (gsm) and preferably about 5 to about 6 gsm. The practical amount of color-forming materials is controlled by economic considerations, functional parameters and desired handling characteristics of the coated sheets.

DESCRIPTION OF THE PREFERRED EMBODIMENTS

In the following examples, general procedures for preparing certain bis(indolyl)ethylenes of formula (I) are described; the examples are not intended to be exhaustive and the moieties, as previously defined, are all eligible for use in any combination in preparing the compounds. Unless otherwise noted, all measurements, percentages and parts are by weight.

Satisfactory spectroscopic data were obtained for the new compounds synthesized.

EXAMPLE 1

Preparation of 1,1-bis(1-ethyl-2-methylindole-3-yl) ethylene

[Table 3, Entry 1]

1-ethyl-2-methylindole (16.0 g, 0.1 mole) and finely powdered zinc chloride (7.0 g, 0.05 mole) were placed in a 250 ml round bottom flask equipped with a dropping funnel, magnetic stirrer and a reflux condenser carrying a drying tube. 1,2-dichloroethane (50 ml) was added, followed by acetic anhydride (10.2 g, 0.1 mole) in 1,2-dichloroethane (30 ml). Then, the reaction mixture was refluxed with stirring. After one hour, GC analysis of the reaction mixture indicated that almost all the starting indole had been used up. The reaction mixture was cooled to room temperature; treated with water (150 ml) to remove most of the zinc salts; the organic layer separated, washed with 10% aqueous sodium hydroxide and brine; dried over anhydrous magnesium sulfate; filtered and the filtrate concentrated under reduced pressure. The residue was dissolved in methanol and cooled in an ice bath. The precipitated solid was isolated and recrystallized from toluene/methanol. Yield (1st crop): 10.3 g (60%), M.P.: 179°-181° C.

The calculated analysis for $C_{24}H_{26}N_2$, the title compound, is C, 84.17%; H, 7.65%; and N, 8.18%. Found on analysis: C, 83.08%; H, 7.68%; and N, 7.88%.

EXAMPLE 2

Preparation of 1,1-bis(1-ethyl-2-methylindole-3-yl)ethylene

[Table 3, Entry 1]

A mixture of 1-ethyl-2-methylindole (15.9 g, 0.1 mole) and acetyl chloride (9.4 g, 0.12 mole) was stirred at room temperature for 20 hours. Then, water (100 ml) was added to the reaction mixture and the resulting grains were filtered and dried. The dried product was recrystallized from toluene/methanol. Yield: 13.0 g (77.0%). M.P.: 183°-185° C. IR (KBr) spectrum was identical to that of the product in Example 1.

EXAMPLE 3

Preparation of 1,1-bis(1-ethyl-2-methylindole-3-yl)ethylene

[Table 2, Entry 2]

A mixture of 1-ethyl-2-methylindole (15.9 g, 0.1 mole), acetyl chloride (2.0 g, 0.025 mole) and acetic anhydride (15 ml) was stirred at 50°-52° C. for 8 hours. Then, the reaction mixture was cooled to room temperature and poured into ice, water and sodium hydroxide (10%, 50 ml). After stirring for 20 minutes, the precipitated solid was filtered off, washed with water, refluxed with methanol for 1 hour and cooled. The solid was filtered, washed with methanol and dried. Yield of the product: 16.5 g (96%), pale yellow powder, m.p.: 179°-182° C. IR(KBr) spectrum was identical to that of the product in Example 1.

EXAMPLE 4

Preparation of 1,1-bis(1-ethyl-2-methylindole-3-yl)-2-phenylethylene

[Table 3, Entry 9]

A mixture of 1-ethyl-2-methylindole (159.0 g, 1 mole), phenacetyl chloride (185.4 g, 1.2 moles) and 1,2-dichloroethane (500 ml) was stirred at 45°-50° C. for 20 hours. Then, the reaction mixture was cooled to room temperature and stirred with ice, water and sodium hydroxide (10%, 600 ml) for 20 minutes. The organic layer was separated, washed with water, dried and concentrated. The residue was refluxed with methanol (1 liter) for 1 hour and cooled. The solid precipitated, was filtered off, washed twice with methanol and dried. Yield of the product: 157 g (75%), white powder, m.p.: 157°-159° C.

The calculated analysis for $C_{30}H_{30}N_2$, the title compound, is C, 86.07%; H, 7.24%; and N, 6.69%. Found on analysis: C, 86.31%; H, 7.08; and N, 6.65%.

EXAMPLE 5

Preparation of 1,1-bis(1-ethyl-2-phenylindole-3-yl)-ethylene

[Table 3, Entry 10]

A mixture of 1-ethyl-2-phenylindole (110.5 g, 0.5 mole) acetyl chloride (78.5 g, 1 mole) and 1,2-dichloroethane (200 ml) was stirred at 50°-55° C. for 20 hours. After cooling to room temperature, the reaction mixture was stirred vigorously with ice, water and sodium hydroxide (10%, 500 ml) for 20 minutes. The organic layer was separated, washed with water, dried and concentrated. The residue was refluxed with methanol (300 ml) and cooled. The resulting solid mass was filtered off, dried and pulverized. The pulverized product was refluxed with isopropanol (30 ml) for 1 hour, cooled, filtered and the residue washed with methanol (200 ml) and dried. Yield of the product: 104 g (89%), pale brown powder, m.p.: 165°-167° C.

The calculated analysis for $C_{34}H_{30}N_2$, the title compound, is C, 87.50%; H, 6.49; and N, 6.00%. Found on analysis: C, 87.72%; H, 6.55%; and N, 6.00%.

EXAMPLE 6

Preparation of 1,1-bis(1-n-octyl-2-phenylindole-3-yl)ethylene

[Table 3, Entry 12]

A mixture of 1-n-octyl-2-phenylindole (122.0 g, 0.4 mole) and acetyl chloride (37.7 g, 0.48 mole) was stirred at 50°-55° C. for 18 hours. TLC analysis of the reaction mixture showed the presence of starting indole. The reaction mixture was stirred with more acetyl chloride (15.7 g, 0.2 mole) for 24 hours. Then, water (3 liters) was added to the reaction mixture, followed by extraction with toluene (300 ml). The toluene extract was washed twice with hot water, dried over anhydrous sodium sulfate, filtered and the filtrate concentrated. The residue was chromatographed on alumina with toluene as eluent. The desired fractions were collected, combined and concentrated under reduced pressure. Yield: 115 g (45%) Pale Brown Oil.

The calculated analysis for $C_{46}H_{54}N_2$, the title compound, is C, 87.00%; H, 8.59%; and N, 4.41%. Found on analysis: C, 87.10%; H, 8.58%; and N, 4.18%.

EXAMPLE 7

Preparation of 1,1-bis(2,5-dimethyl-1-ethylindole-3-yl)ethylene

[Table 3, Entry 13]

A mixture of 2,5-dimethyl-1-ethylindole (95.2 g, 0.55 mole) and acetyl chloride (86.4 g, 1.1 moles) was stirred at room temperature for 20 hours. Then, the reaction mixture was poured into ice, water and sodium hydroxide (10%, 300 ml) and stirred vigorously for 20 minutes. The precipitated solid was filtered off, washed with water, refluxed with methanol (500 ml) for 1 hour and cooled. The solid was filtered, washed with methanol and dried. Yield of the product: 94.0 g (92%), pale grey powder, m.p.: 125°-127° C.

The calculated analysis for $C_{26}H_{30}N_2$, the title compound, is C, 84.26%; H, 8.18%; and N, 7.56%. Found on analysis: C, 84.11%; H, 8.36%; and N, 7.53%.

EXAMPLE 8

Preparation of 1,1-bis(2,7-dimethyl-1-ethylindole-3-yl)ethylene

[Table 3, Entry 17]

A mixture of 2,7-dimethyl-1-ethylindole (65.7 g, 0.38 mole) and acetyl chloride (59.7 g, 0.76 mole) was stirred at room temperature for 20 hours. Then, the reaction mixture was added to ice, water and sodium hydroxide (10%, 300 ml) and stirred for 20 minutes. The solid precipitated was worked-up as in Example 6. Yield of the product: 63.0 g (90%), grey powder, m.p.: 160°-161° C.

The calculated analysis for $C_{26}H_{30}N_2$, the title compound, is C, 84.26%; H, 8.18%; and N, 7.56%. Found on analysis: C, 84.50%; H, 8.02%; and N, 7.58%.

EXAMPLE 9

Preparation of 3-acetyl-1-ethyl-2-methylindole (K5)

Phosphoryl chloride (33.7 g, 21.0 ml, 0.22 mole) was added dropwise to vigorously stirred N,N-dimethylacetamide (19.2 g, 20.5 ml, 0.22 mole) cooled in an ice/salt bath, keeping the temperature of the reaction mixture between 10° and 20° C. during the addition. Then, the reaction mixture was stirred for 30 minutes as it warmed to room temperature. 1,2-dichloroethane (50 ml) was added to the reaction mixture, cooled in an ice/salt bath and followed by the addition of 1-ethyl-2-methylindole (32.0 g, 0.20 mole) in 1,2-dichloroethane (30 ml.) while the reaction mixture was kept at 5° C. The reaction mixture was then refluxed for one hour, cooled to room temperature, stirred with aqueous sodium hydroxide (10%) and the organic layer was separated. The organic layer was washed with aqueous sodium hydroxide (10%) and then with brine (2×), dried and filtered, and the filtrate concentrated. The residue was chromatographed on silica gel using toluene:acetone::4:1 as eluent. The fractions containing the product were collected, combined and concentrated. The residue was recrystallized from toluene/petroleum ether. Yield: −33.5 g (83%), pale yellow solid, m.p.: −90°-92° C.

The calculated analysis for $C_{13}H_{15}NO$, the title compound, is C, 77:58%; H, 7.51%; N, 6.96%; and O, 7.95%. Found on analysis: C, 77.71%; H, 7.45%; and N, 6.94%.

EXAMPLE 10

Preparation of 1-(1-ethyl-2-methylindole-3-yl)-1-(1-ethyl-2-methyl-6,7-benzoindole-3-yl)-ethylene

[Table 3, Entry 21]

Phosphoryl chloride (1.6 g, 0.01 mole) was added slowly to a well-stirred solution of 3-acetyl-1-ethyl-2-methylindole (2.2 g, 0.011 mole) in 1,2-dichloroethane (10 ml) cooled in an ice/salt bath. Stirring was continued for one hour as the reaction mixture warmed to room temperature. Then, 1-ethyl-2-methyl-6,7-benzoindole (2.1 g, 0.01 mole) was added and the reaction mixture was refluxed for one hour, cooled to room temperature, treated with aqueous sodium hydroxide (10%, 30 ml); the organic layer was separated, washed with water, dried and concentrated. The residue was chromatographed on silica gel using toluene as eluent. Fractions containing the product were collected, combined and concentrated. The residue was recrystallized from isopropanol. Yield: 3.1 g (80%), yellow solid, m.p.: −138°-140° C.

The calculated analysis for $C_{28}H_{28}N_2$, the title compound, is C, 85.67%; H, 7.19%; and N, 7.14%. Found on analysis: C, 85.81%; H, 7.26%; and N, 7.19%.

EXAMPLE 11

Preparation of 1-(1-ethyl-2-methylindole-3-yl)-1-(1-β-methoxyethyl-2-methylindole-3-yl)-ethylene

[Table 3, Entry 22]

3-acetyl-1-ethyl-2-methylindole (4.4 g, 0.022 mole) was dissolved in 1,2-dichloroethane (30 ml) and the solution was cooled in an ice/salt bath. Phosphoryl chloride (3.1 g, 0.02 mole) was added and the reaction mixture was stirred for 30 minutes as it warmed to room temperature. Then, 1-(β-methoxyethyl)-2-methylindole (3.8 g, 0.02 mole) in 1,2-dichloroethane (10 ml) was added and the reaction mixture was stirred overnight at room temperature. After refluxing for one hour, the reaction mixture was cooled; poured into ice, water and sodium hydroxide (10%, 100 ml); stirred for 20 minutes and the organic layer separated. The organic layer was washed with water, dried and concentrated under reduced pressure. The residue was chromatographed on silica gel using toluene as eluent. The fractions containing the product were collected, combined and concentrated. The residue was recrystallized from toluene/methanol. Yield: 5.5 g (74%), pale yellow solid, m.p.: −123°-125° C.

The calculated analysis for $C_{25}H_{28}N_2O$, the title compound, is C, 80.61%; H, 7.58%; N, 7.52%; and O, 4.29%. Found on analysis: C, 80.82%; H, 7.65%; and N, 7.50%.

EXAMPLE 12

Example of pressure-Sensitive Record Material

Formulations and techniques for the preparation of carbonless copy paper are well known in the art, for example, as disclosed in U.S. Pat. Nos. 3,627,581; 3,775,424; and 3,853,869 incorporated herein by reference. CF sheets used with the CB sheets to form a manifold assembly are well known in the art. Substrate sheets containing oil-soluble metal salts of phenol-formaldehyde novolak resins of the type disclosed in U.S. Pat. Nos. 3,675,935; 3,732,120; and 3,737,410 are exemplary thereof. A typical example of a suitable acidic resin is a zinc modified, oil-soluble phenol-formaldehyde resin such as the zinc salt of a para-octylphenol-formaldehyde resin or the zinc salt of a para-phenylphenol-formaldehyde resin.

| Color former solution: | Parts |
|---|---|
| bis indolylethylene | 5.6 |
| ex. (1,1-bis(1-ethyl-2-methyl-3-indolyl)ethylene | |
| $C_{10}$-$C_{15}$ alkylbenzene | 130.0 |
| ex. Alkylate 215 | |
| (ethylphenyl)phenylmethane | 70.0 |

The color former solution is emulsified into a mixture of 35 parts of 10% EMA 31 [ethylene-maleic anhydride copolymer with a molecular weight range of 75,000 to 90,000 (Monsanto)] in water, 32 parts of 20% EMA 1103 [ethylene maleic anhydride copolymer with a molecular weight range of 5,000 to 7,000 (Monsanto)] in water, 133 parts water, 10 parts urea, and 1 part resorcinol, adjusted to pH 3.5. Following emulsification 29 parts 37% formaldehyde is added and the mixture placed in a 55° C. water bath with stirring. After two hours, with stirring maintained, the temperature of the water bath is allowed to equilibrate with ambient temperature. The capsules are used to prepare a paper coating slurry.

| | Parts Wet | Parts Dry |
|---|---|---|
| capsule slurry | 80 | 40 |
| wheat starch granules | 10 | 10 |
| etherified corn starch binder | 40 | 4 |
| ex. Penford 230, 10% | | |
| (Penwick and Ford Ltd.) | | |
| water | 100 | — |

The slurries are applied to a paper base and drawn down with a No. 12 wire wound coating rod and the coatings dried. The resulting CB coatings are coupled with a sheet comprising a zinc-modified phenolic resin as disclosed in U.S. Pat. Nos. 3,732,120 and 3,737,410. Upon pressure contact, a visible image forms corresponding to the localized contact. Dyes can be versatilely mixed for color customization.

EXAMPLE 13

Example of Heat-Sensitive Record Material

The coating is prepared by milling the components in an aqueous solution of the binder until a particle size of between 1 and 10 microns is achieved. The milling is accomplished in an attritor, small media mill, or other suitable dispensing vehicle. The desired average particle size is 1 to 3 microns.

Separate dispersions of chromogenic compound, acidic developer material, and sensitizer are prepared.

| | Parts |
|---|---|
| Chromogenic Dispersion A | |
| bis-indolylethylene | 39.10 |
| ex. 1,1-bis(2,5-dimethyl-1-ethyl-3-indolyl)ethylene of Example 7 | |
| binder, 20% polyvinylalcohol in water | 28.12 |
| water | 45.00 |
| defoamer and dispersing agent | 00.28 |
| ex Nopko NDW (sulfonated castor oil of Nopko Chemical Co.) | |
| Surfynol 104 | 10.60 |
| (a ditertiary acetylene glycol surface active agent) | |
| Acidic Developer Material Dispersion B | |
| acidic developer material | 13.60 |
| ex. 4,4'-isopropylidenediphenol | |
| binder, 10% polyvinylalochol in water | 24.00 |
| water | 42.35 |
| defoamer, Nopko NDW | 00.05 |
| Surfynol | 00.60 |
| Sensitizer Dispersion C (optional) | |
| sensitizer | 13.60 |
| ex. phenyl-1-hydroxy-2-naphthoate or 1,2-diphenoxyethane U.S. Pat. No. 4,531,140 | |
| binder, 10% polyvinylalcohol in water | 24.00 |
| water | 42.35 |
| defoamer, Nopko NDW | 00.05 |
| Surfynol | 00.60 |

The above separate dispersions, A, B, and C, can be combined as follows, and optionally include zinc stearate, 21% dispersion, urea formaldehyde resin, and micronized silica.

The above dispersions are combined 0.6 parts A, 4.9 parts B, 3.3 parts C, along with 1.4 parts zinc stearate dispersion, 4.3 parts water, 1.9 parts polyvinylalcohol and 0.6 parts urea formaldehyde resin. This mix is applied to paper and dried yielding a dry coat weight of 5.2 to 5.9 gsm. The resultant paper is sensitive to applied heat such as via a thermal print head.

What is claimed:

1. A method for the manufacture of bis-(indolyl)ethylenes of the formula

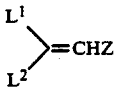

wherein each $L^1$ and $L^2$ is the same or different and is each independently selected from indole moieties (J1) through (J4),

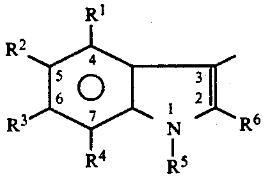

(J1)

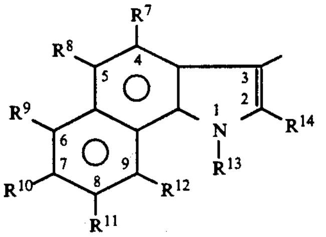

(J2)

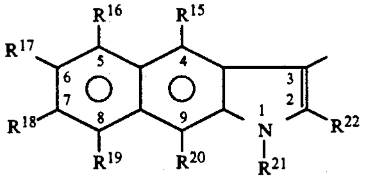

(J3)

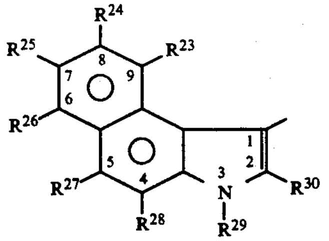

(J4)

wherein in each (J1) through (J4) each $R^5$, $R^6$, $R^{13}$, $R^{14}$, $R^{21}$, $R^{22}$, $R^{29}$ and $R^{30}$ need not be the same and is each independently selected from hydrogen, alkyl ($C_1$-$C_8$), cycloalkyl, aroxyalkyl, alkoxyalkyl, substituted aryl, and unsubstituted aryl;

wherein each $R^1$, $R^2$, $R^3$, $R^4$, $R^7$, $R^8$, $R^9$, $R^{10}$, $R^{11}$, $R^{12}$, $R^{15}$, $R^{16}$, $R^{17}$, $R^{18}$, $R^{19}$, $R^{20}$, $R^{23}$, $R^{24}$, $R^{25}$, $R^{26}$, $R^{27}$ and $R^{28}$ need not be the same and is each independently selected from hydrogen, alkyl ($C_1$-$C_8$), cycloalkyl, substituted or unsubstituted aryl, halogen, alkoxy ($C_1$-$C_8$), aroxy, cycloalkoxy, dialkylamino, alkylcycloalkylamino, dicycloalkylamino,

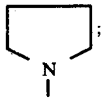 ; 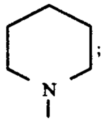 ; 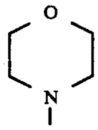 and 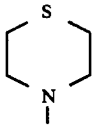 , wherein Z is hydrogen, alkyl ($C_1$-$C_8$), substituted or unsubstituted aryl, aralkyl, aroxyalkyl, alkoxyalkyl and halogen, said method comprising:

reacting indoles corresponding to each respective $L^1$ and $L^2$ with acetic anhydride in the presence of an acid, selected from sulfonic acid, acid chloride, and Lewis acid, in a solvent.

2. The method according to claim 1 wherein the solvent is a halogenated organic solvent.

3. A method for the manufacture of bis-(indolyl)ethylenes of the formula

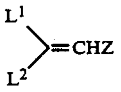

(I)

wherein each $L^1$ and $L^2$ is the same or different and is each independently selected from indole moieties (J1) through (J4),

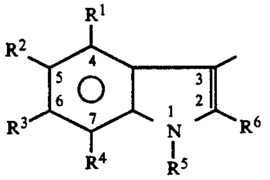

(J1)

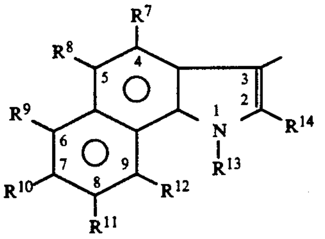

(J2)

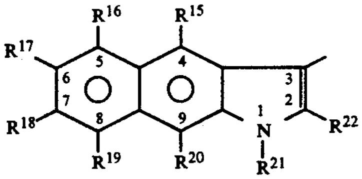

(J3)

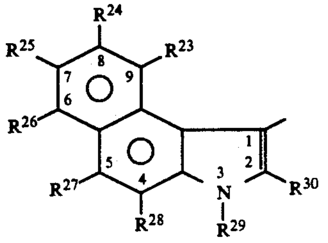

(J4)

wherein in (J1) through (J4) each of $R^5$, $R^6$, $R^{13}$, $R^{14}$, $R^{21}$, $R^{22}$, $R^{29}$ and $R^{30}$ need not be the same and is each independently selected from hydrogen, alkyl ($C_1$–$C_8$), cycloalkyl, aroxyolkyl, alkoxyalkyl, substituted aryl, and unsubstituted aryl, wherein each $R^1$, $R^2$, $R^3$, $R^4$, $R^7$, $R^8$, $R^9$, $R^{10}$, $R^{11}$, $R^{12}$, $R^{15}$, $R^{16}$, $R^{17}$, $R^{18}$, $R^{19}$, $R^{20}$, $R^{23}$, $R^{24}$, $R^{25}$, $R^{26}$, $R^{27}$ and $R^{28}$ need not be the same and is independently selected from hydrogen, alkyl ($C_1$–$C_8$), cycloalkyl, substituted or unsubstituted aryl, halogen, alkoxy ($C_1$–$C_8$), aroxy, cycloalkoxy, dialkylamino including symmetrical and unsymmetrical alkyl groups with one to eight carbons, alkylcycloalkylamino, dicycloalkylamino,

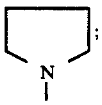; 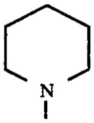; 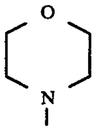 and 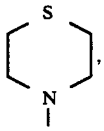, wherein z is hydrogen, alkyl ($C_1$–$C_8$), substituted or unsubstituted aryl, aralkyl, aroxyalkyl, alkoxyalkyl and halogen, said method comprising:

condensing acylindoles (K1) through (K4) with indoles (J1) through (J4) using Vilsmeier reagents with or without solvent,

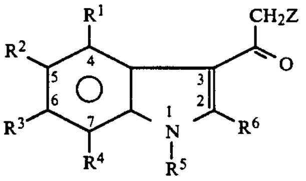

(K1)

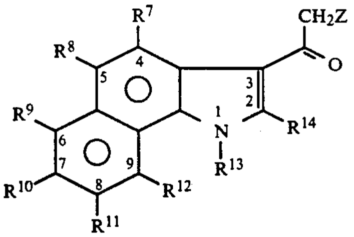

(K2)

-continued

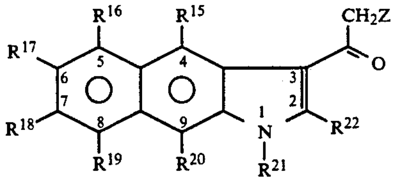

(K3)

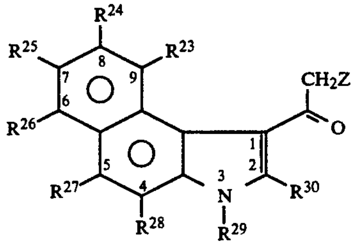

(K4)

wherein in (K1) through (K4) each of $R^5$, $R^6$, $R^{13}$, $R^{14}$, $R^{21}$, $R^{22}$, $R^{29}$ and $R^{30}$ need not be the same and is each independently selected from hydrogen, alkyl ($C_1$–$C_8$), cycloalkyl, alkylaroxy, alkylalkoxy, substituted aryl, and unsubstituted aryl, such as phenyl, naphthyl, or heterocyclyl, each $R^1$, $R^2$, $R^3$, $R^4$, $R^7$, $R^8$, $R^9$, $R^{10}$, $R^{11}$, $R^{12}$, $R^{15}$, $R^{16}$, $R^{17}$, $R^{18}$, $R^{19}$, $R^{20}$, $R^{23}$, $R^{24}$, $R^{25}$, $R^{26}$, $R^{27}$, and $R^{28}$ need not be the same and is independently selected from hydrogen, alkyl ($C_1$–$C_8$), cycloalkyl, substituted or unsubstituted aryl, halogen, alkoxy ($C_1$–$C_8$), aroxy, cycloalkoxy, dialkylamino including symmetrical and unsymmetrical alkyl groups with one to eight carbons, alkylcycloalkylamino, dicycloalkylamino,

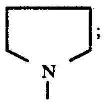; 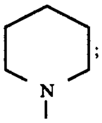; 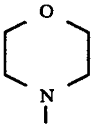 and 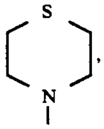, wherein z is hydrogen, alkyl ($C_1$–$C_8$), substituted or unsubstituted aryl, aralkyl, aroxyalkyl, alkoxyalkyl and halogen.

4. The method according to claim 3 wherein the Vilsmeier reagents are selected from the group consisting of phosphoryl chloride, phosgene, oxalyl chloride, benzoyl chloride, alkane sulfonyl chloride, arene sulfonyl chloride, alkylchloroformate, and arylchloroformate.

* * * * *